(12) United States Patent
Lin et al.

(10) Patent No.: US 7,560,239 B2
(45) Date of Patent: Jul. 14, 2009

(54) HOMOGENEOUS ENZYME IMMUNOASSAY FOR SIMULTANEOUS DETECTION OF MULTIPLE ANALYTES

(75) Inventors: Marie Lin, Cupertino, CA (US); Tom Chia, Cupertino, CA (US); Chiu Chin Chang, Sunnyvale, CA (US)

(73) Assignee: Lin-Zhi International Inc., Sunnyvale, CA (US)

( * ) Notice: Subject to any disclaimer, the term of this patent is extended or adjusted under 35 U.S.C. 154(b) by 1325 days.

(21) Appl. No.: 10/163,018

(22) Filed: Jun. 4, 2002

(65) Prior Publication Data

US 2003/0224373 A1   Dec. 4, 2003

(51) Int. Cl.
  *G01N 33/00* (2006.01)
(52) U.S. Cl. .......................... 435/7.1; 435/7.4; 435/7.9; 435/7.92; 435/7.93; 435/26; 436/501; 436/518; 436/536; 424/130.1
(58) Field of Classification Search .................. 435/7.1, 435/7.4, 7.9, 7.92, 7.93, 26; 436/501, 518, 436/536; 424/130.1
See application file for complete search history.

(56) References Cited

U.S. PATENT DOCUMENTS

| | | | |
|---|---|---|---|
| 3,817,837 A | | 6/1974 | Rubenstein et al. |
| 3,875,011 A | * | 4/1975 | Rubenstein et al. .......... 435/188 |
| 4,446,065 A | | 5/1984 | Lin et al. |
| 4,923,819 A | | 5/1990 | Fernandez et al. |
| 5,135,863 A | * | 8/1992 | Hu et al. ..................... 435/188 |
| 5,187,106 A | | 2/1993 | Fritzsche et al. |
| 5,206,179 A | | 4/1993 | Ramsey |
| 5,286,452 A | | 2/1994 | Hansen |
| 5,328,828 A | | 7/1994 | Hu et al. |
| 5,501,987 A | | 3/1996 | Ordonez et al. |
| 5,756,709 A | | 5/1998 | Nelson et al. |
| 5,834,181 A | | 11/1998 | Shuber |
| 5,863,401 A | | 1/1999 | Chen |
| 5,958,202 A | | 9/1999 | Regnier et al. |
| 6,033,890 A | * | 3/2000 | Jakobovits et al. .......... 435/190 |
| 6,090,567 A | * | 7/2000 | Jakobovits et al. ........... 435/7.9 |
| 6,124,138 A | | 9/2000 | Woudenberg et al. |
| 6,197,503 B1 | | 3/2001 | Vo-Dinh et al. |
| 6,294,062 B1 | | 9/2001 | Buck, Jr. et al. |

OTHER PUBLICATIONS

Huang et al. (Analytical Chemistry, 1996, 68, 1646-1650).*
Kim et al. (Analytical Biochemistry, 1994, 218(1), 14-19).*
Srinivas (Biomedical Chromatography, 18, pp. 759-784, 2004).*
Peterson et al. (Forensic Science International, 73, 1995, 183-196).*
Hallowell et al. (Journal of Clinical Laboratory Analysis, 1990, vol. 4, No. 1, pp. 64-73, Abstract Only).*
Huang et al. (Analytical Chemistry, 1996, vol. 68, pp. 1646-1650).*
Levy, H. R., "Glucose-6.-Phosphate Dehydrogenases," Advances in Enzymology 48:97-192, (1979).
Bhadbhade, M. M. et al., "Sequence Identity Between A Lysine Containing Peptide From Leuconostoc Mesenteroides Glucose-6—Phosphate Dehydrogenase And An Active Site Peptide From Human Erythrocyte Glucose-6—Phosphate Dehydrogenase"; FEBS Left. 211:243-246. (Jan. 1987).
Jeffery et al., Glucose-6-.Phosphate Dehydrogenase From Saccharomyces Cerevisiae: Characterization Of A Reactive Lysine Residue Labeled With Acetylsalicylic Acid; Biochem. 24:666-671, (1985).
EMIT® 11 "Monoclonal Amphetamine/Methamphetamine Assay" package insert by Syva/ Behring, (1993).
Ullman et al; "Luminescent Oxygen Channeling Assay (Loci™): Sensitive, Broadly Applicable Homogeneous Immunoassay Method", Clin. Chem., 42/9:1518-1526, (1996).

* cited by examiner

*Primary Examiner*—Lisa V Cook
(74) *Attorney, Agent, or Firm*—Townsend and Townsend and Crew LLP

(57) ABSTRACT

Methods and kits are provided for the simultaneous detection of multiple analytes, i.e. to the determination of whether one or more of a plurality of analytes is present in a sample, particularly the plurality of analytes are structurally unrelated or significantly different, particularly to whether one or more of such analytes is present in a sample in a concentration that is above a predetermined minimum or cutoff value, and particularly for such analytes with different cutoffs. The methods and kits are particularly useful for-screening for the presence of a plurality of drugs (licit and/or illicit), performance-enhancing substances, and other chemicals, and involve a competitive enzyme immunoassay employing one or more conjugates of G6PDH with a plurality of the analytes.

16 Claims, No Drawings

HOMOGENEOUS ENZYME IMMUNOASSAY FOR SIMULTANEOUS DETECTION OF MULTIPLE ANALYTES

BACKGROUND OF THE INVENTION

Field of the Invention

The present invention relates to the simultaneous detection of multiple analytes, i.e. to the determination of whether any of a plurality of analytes is present in a sample, particularly the plurality of analytes of significant structurally difference, and particularly to whether any of such analytes is present in a sample in a concentration that is above a predetermined minimum or cutoff value for each individual analyte. More specifically, the invention is directed to a method for screening biological fluid samples for multiple analytes wherein at least two of the analytes simultaneously are to be screened or checked for a presence at different cutoff levels.

There are a number of occasions on which a sample, particularly a sample of a biological fluid obtained from an individual, is to be screened for the presence of one or more analytes, particularly one or more chemical substances. For instance, samples of blood, urine, or another biological fluid from applicants for certain permits or licenses may be checked for the presence of alcohol or illicit drugs. Samples from a driver may be checked for such substances after an accident, or in applying for commercial permits or licenses or their renewals. Samples of individuals undergoing a drug treatment program may be screened for the presence of drugs. Samples from athletes may be screened to determine the presence of banned substances such as drugs, steroids, or other performance-enhancing substances.

Such screening may be done for substances other than illicit drugs or the like. For instance, patients admitted to a hospital may need to be checked for both licit and illicit drugs, including tranquilizers, and the like, so that appropriate treatment may be given or precautions taken. Such patients may be unconscious or suffering from trauma and may be unable to volunteer, or may be unwilling to provide, information about ingestion of certain substances. Checking of employees, workers or other persons at a certain location may need to be conducted to ascertain whether the individual has been exposed to a plurality of chemicals used in or around the workplace, or released into the environment.

In all the above cases, the screening is typically done to determine whether the substances in question are present in the bodies (that is, in samples of biological fluids) of the individuals in question. Typically the screening is to be conducted not only to determine whether detectable amounts of the substances in question are present in the sample, but whether a particular substance is present in an amount greater than a predetermined level. Such a level is also known as a "cutoff level". These levels may be set by an organizational rule, e.g. an employer's rule, or by a law, for example, a maximum level of blood alcohol for one driving a vehicle, or a maximum amount of a steroid or other performance-enhancing substance for one to compete in an athletic event.

Currently such screening is done by subjecting the sample to a series of individual tests for each substance or family of substances whose presence is sought to be determined. In such tests the predetermined (cutoff) minimum or maximum level may well be different for each substance. For instance, in tests conducted on athletes, the cutoff level may be one concentration for steroids and another for a prohibited amino acid nutritional supplement. Testing of a patient admitted to a hospital may be needed for very different substances that the patient may have ingested, and whose presence at different levels may be required to determine appropriate treatment or for other purposes. Typical screens for multiple analytes in such situations can be time-consuming.

U.S. Pat. No. 3,817,837 provides a typical method for conducting assays for screening for the presence of individual analytes in a sample, using an enzyme amplification assay, and describes procedures for detecting the presence of a number of different types of chemical substances, including licit and illicit drugs, even at low concentrations. The procedure involves a competitive binding assay of the drug, either per se or in a form that contains a linking group that can bind to the enzyme used in the procedure. Inhibition of enzymatic activity is utilized to determine the presence and quantity of the chemical substance present in the sample. The method is frequently referred as the Enzyme Multiplied Immunoassay Technology (EMIT). This patent is hereby incorporated herein, in its entirety.

While the technique from U.S. Pat. No. 3,817,837 substantially improved the efficiency of testing various analytes, it does not resolve the problem of simultaneously analyzing multiple analytes in a sample. Multiple tests (single analyte tests) for each and every sample could add up to a significant cost and labor, and understandably, required a long period of time to complete. It would be advantageous to have available a method whereby a sample could be simultaneously screened for the presence of such multiple analytes in a single assay. If the screen showed none of the analytes present at the minimum predetermined concentrations, no further testing of the sample would be needed for any of these substances. Only the screen showed some of the tested substances to be present at the relevant level, further testing then would be called for. The impact of having such a streamlined screening method can be enormous when mass screening, such as pre-employment drug tests for new recruits of Military Service men and women, is implicated.

U.S. Pat. No. 5,501,987 disclosed a dual analyte immunoassay for detection of amphetamine and methamphetamine in a sample using a pair of antibodies and one single labeled derivative of one of the two analytes, most preferably amphetamine. The mechanism of detection is by agglutination. The analytes are structurally related amphetamines, and the cutoff level for either compound is at the same level.

U.S. Pat. No. 5,328,828 described compositions and methods where a pair of antibodies and a pair of conjugates with functionally similar label were used to determine the presence of amphetamines in a sample suspected of containing amphetamine and/or methamphetamine. Again, the analytes of interest are two structurally closely related compounds, and the cutoff concentration for the two substances is one single level.

The above stated patents provided valuable techniques for assaying two structurally close-related analytes in a sample of biological fluid. However, the structure and cutoff concentration of each such drug for which determination may be needed tend to be different in routine situations. For example, The guidelines provided by The National Institute of Drugs of Abuse (NIDA) and The Substance Abuse and Mental Health Services Administration (SAMHSA) recommend the following cutoff levels for the drugs of abuse screening by immunoassays:

| Drug Category | Cutoff Concentration |
| --- | --- |
| Amphetamines | 1000 ng/mL |
| Opiates | 300 ng/mL |
| Phencyclidine | 25 ng/mL |
| Cocaine | 300 ng/mL |
| Cannabinoids | 50 ng/mL |

While the above patents provided very useful information, none presented a solution to the problem of simultaneously assaying for multiple analytes having significantly different structures and/or of different cutoff values. It would be advantageous to have available a method whereby a sample could be simultaneously screened for the presence of such multiple analytes with certain specific, relevant cutoffs in a single assay. If the screen result is negative, indicating none of the analytes present at their minimum predetermined concentrations, no further testing of the sample would be needed for any of these substances. If the screen is positive, indicating one or more of the tested substances to be present at the relevant level, further testing would then be called for.

Various, other methods for multi-analyte analysis have been reported which included homogeneous fluoro-immunoassays (U.S. Pat. No. 5,187,106), fluorescence polarization at multiple wavelengths for determining multiple analytes (U.S. Pat. No. 5,206,179), electrochemical immunoassay (U.S. Pat. No. 6,294,062), luminescent oxygen channeling immunoassay (Clin. Chem.,42/9:1518-1526, 1996), time-resolved fluorescence multiplex immunoassay (U.S. Pat. No. 4,923,8196), multianalyte capillary electrophoresis assays (U.S. Pat. Nos. 5,863,401 and 5,958,202), refractive indexed optical flow particle analysis (U.S. Pat. No. 5,286,452), and biochip technology or alike (U.S. Pat. Nos. 5,834,181; 6,197,503 B1; 6,124,138;), etc.

SUMMARY OF THE INVENTION

This invention comprises a novel homogeneous enzyme immunoassay for the simultaneous detection of two or more structurally different analytes in a biological fluid. The assays involve a method for detecting the presence of one or more non-serologically cross-reactive analyte types in a sample using a competitive homogeneous assay: where the assay detects a plurality of different analyte types that are non-serologically cross-reactive and, where the assay involves analyte and receptor binding pairs such that the presence of one or more different analyte types is determined by enzyme activity reflecting the concentration of analyte when present in excess of a predetermined concentration of the cutoff. The method comprising the steps of: combining in an aqueous medium the following compositions, (a) Glucose-6-phosphate dehydrogenase (G6PDH)-analyte binding pair member conjugates covalently linked to a plurality of different analyte binding pair members of which at least two are non-serologically cross-reactive; (b) receptors reactive to both analytes and the G6PDH-analyte binding pair member conjugates; and, (c) a sample to be tested for the presence of any of the plurality of analyte types and, detecting increased G6PDH activity in the aqueous medium due to competitive binding of the receptors with the analytes in the sample.

The method further provides that concentrations of G6PDH-analyte binding pair member conjugates and of the receptors are adjusted in the aqueous mixture so that the enzyme rate at the predetermined cutoff concentrations is approximately the same (i.e., within 5%, preferably, within 4%, and more preferably, within 3% of each other) for the different analyte types whose presence is to be detected; wherein the G6PDH is deactivated by from about 20% to about 85% resulting from the covalent linkage to the analyte binding pair member; and wherein the deactivated G6PDH is inhibited by from about 20% to about 85% when bound to the receptors. The receptors may be antibodies.

The invention further provides for the above method where at least two of the analyte types have a different cutoff concentration marking a predetermined concentration above which a positive signal is generated. The conjugates may either comprise individual G6PDH molecules covalently linked to a plurality of different types of analytes or the conjugates may comprise individual G6PDH molecules covalently linked to a plurality of identical analyte types.

In another embodiment the assays of this invention have at least two of the analytes that are non-serologically cross-reactive to each other. The analytes include those selected from group consisting of: licit and illicit drugs, sugars, amino acids, peptides, nucleic acids, nucleosides, nucleotides, vitamins, hormones, steroids, toxins, chemical and biological warfare agents, pesticides, and industrial chemicals, and analogs, derivatives and metabolites thereof. The analytes may also be selected from the group consisting of licit and illicit drugs and analogs, derivatives and metabolites thereof. More specifically the analytes may be opium, opioid analgesics, amphetamines, cocaine, methadone, alkaloids, catecholamines, methylendioxyamphetamines (MDMA, MDA, and MDEA, etc.), PCP, propoxyphene, methaqualone, barbiturates, benzodiazepines, tricyclic antidepressants, tranquilizers, tetrahydrocannabinol, LSD, ketamine, GHB, and other drugs of abuse, including amino acids, hormones, and steroids, and analogs, metabolites, and derivatives thereof. In another embodiment the assay may involve situations in which at least two of the analytes are selected from drugs of abuse having two different predetermined cutoff concentrations. Alternatively, the analytes may be selected from the group consisting of: barbiturates, tricyclic anti-depressants, tranquilizers, and benzodiazepines, and analogs, metabolites, and derivatives thereof. Further the analytes may be selected from the group consisting of alkaloids, peptides, nucleic acids, nucleosides, nucleotides, vitamins, hormones, food supplements, sugars, steroids, amino acids, and other performance-enhancing agents, and analogs, metabolites, and derivatives thereof. The analytes may also be selected from group consisting of chemical and biological warfare agents, toxins, pesticides, herbicides, and industrial chemicals and pollutants.

In some embodiments the G6PDH is deactivated by from about 20 to about 60% and/or the enzyme activity of the deactivated G6PDH-analyte conjugate is inhibited by from about 40 to about 80%. In other embodiments the G6PDH is a recombinant G6PDH.

In other embodiments the assay are prepared as kits for testing the presence of analytes in a sample using a competitive homogeneous assay where the assay simultaneously detects the presence of a plurality of different analyte types that are non-serologically cross-reactive said kits comprising: (a) a container containing a mixture of G6PDH-analyte binding pair member conjugates covalently linked to one or more different analytes types; and, (b) a container containing receptors reactive to both analytes and the G6PDH-analyte binding pair members; where the concentrations of the said conjugates and receptors are adjusted in the containers to yield approximately the same enzyme rate for each analyte when present at its predetermined cutoff concentration, so that sample containing one or more of a plurality of the analytes in an excess of its predetermined cutoff concentration can be identified. In an alternative embodiment, the kits are used to simultaneously detect a plurality of analytes among which at least two having different predetermined cutoff concentrations, with which any of the analytes when present in an excess of their predetermined cutoff concentrations can be detected.

In an alternative embodiment, the kit comprises antibodies reactive to the plurality of analytes. The kits of this invention embrace the specifics outlined above for the methods.

DEFINITIONS

As used herein:

"Antibody" refers to a protein functionally defined as a binding protein and structurally defined as comprising an amino acid sequence that is recognized by one of skill as being derived from the framework region of an immunoglobulin encoding gene of an animal producing antibodies. It includes whole antibody, functional fragments, modification or derivatives of the antibody. It can also be genetically manipulated product, or chimeric antibody.

"G6PDH" refers to the enzyme glucose-6-phosphate dehydrogenase, which may be obtained either from natural sources, such as from yeast, bacteria, in native or mutational form or prepared by recombinant methods.

"Analyte" means a substance whose presence is to be determined. "Hapten" is the modified drug or analyte with a proper functional group so that it can be covalently linked to desirable proteins to form an immunogen or an enzyme conjugate, etc. Within the context of the current patent, "analyte" maybe used in substitution for "analyte and/or hapten" for fluidity and verbiage redundancy reduction. It is also equivalent to the word "ligand" used in the U.S. Pat. No. 3,817,837. More specifically, the term when used in the context of a G6PDH-analyte binding pair member conjugate, may include a drug, a metabolite of the drug or a representative epitope.

"Analyte types" refers to distinct molecules which may or may not share common epitopes so that they are serologically cross-reactive. They are structurally distinguishable.

"Approximately the same" in the context of an enzyme rate at a given cutoff concentration is within 5% of each other.

"Competitive assay" means an assay in which labeled ligand (such as the enzyme-linked analyte, or "enzyme-analyte conjugate") competes for antibody or receptor sites with free ligand (such as the analyte present in the sample). The two ligand-species (the "analyte" in the sample and the "enzyme-analyte conjugate") may be added to the antibody or receptor solution simultaneously or sequentially.

"Cutoff level", "concentration of the cutoff" or "cutoff concentration" all refer to a concentration of a given analyte, at or above which the presence of the analyte in the sample is sought to be determined. A cutoff level tends to be a concentration established by a rule or standard of a government agency or of a governing body, for example, a governing body of a sport.

"Deactivation" of an enzyme (in this invention, the enzyme being glucose-6-phosphate dehydrogenase or G6PDH) refers to a decrease in activity of the enzyme in question, i.e. its ability to bind and turn over a substrate (i.e., glucose-6-phosphate, or G6P).

"Drug": Substances commonly included within this category including both licit and illicit drugs, i.e. both substances used for medicinal or pharmaceutical effects as well as substances used for producing narcotic or other addictive properties.

As used herein, the term "drug" may also refer to chemical substances to be determined that are not strictly considered drugs, but that may be ingested by athletes for performance-enhancing effects (including as nutritional substances), and whose presence is thus sought to be determined in screening samples from athletes. Such substances include, for instance, amino acids, steroids, and hormones, etc.

"G6PDH-analyte binding pair member conjugate" refers to a covalent fusion between the glucose-6-phosphate dehydrogenase enzyme and an analyte as defined above.

A "homogeneous assay" is a liquid phase assay that does not involve separation of bound and unbound species in the system.

"Inhibition" of an enzyme refers to a decrease in the relative ability of the enzyme to bind and turn over the substrates as a result of binding of antibodies or receptors to the enzyme-analyte conjugate.

"Receptors reactive to" refer to a member of a specific binding pair, i.e., two different molecules where one of the molecules through chemical or physical means specifically binds to the second molecule. In the context of this invention, the receptors are complementary binding pair members that can inhibit the enzyme activity when bound to the conjugate. In addition to the well-known example of the antigen and antibody specific binding pair, alternative specific binding pairs are exemplified by the following: morphine/opioid peptides and opioid receptors, carbohydrates and lectins, hormone and hormone binding proteins, enzynme substrates/inhibitors/cofactors and enzymes, Vitamin $B_{12}$ and intrinsic factor, Ras and farnesyltansferase (FTase), fibronectin and related peptides and fibrinogen receptor, and the like.

"Non-serologically cross-reactive" refers to compositions that when independently used as an antigen in an animal (such as rabbit, sheep, goat, chicken or mouse, etc) they will generate antisera that only has an ability to specifically bind to the other composition at a rate of less than 10% above background when tested in an immunological assay such as an ELISA.

INCORPORATION BY REFERENCE

All publications and patent applications cited in this specification are herein incorporated by reference as if each individual publication or patent application were specifically and individually indicated to be incorporated by reference.

DETAILED DESCRIPTION OF THE INVENTION

The first step in conducting analyses using this invention is to prepare conjugates of the analytes with the glucose-6-phosphate dehydrogenase enzyme (G6PDH). The conjugation can be achieved via conventional chemical reactions. Among them, the simplest reaction to coupling an analyte (or a hapten) with G6PDH is through the formation of a peptide bond (—$CONH_2$). For example, utilize a carboxylic group on the analyte (or the hapten) to react with the amino group on the G6PDH enzyme (Biochem and Biophys Research Comm, 160:3, pp. 1290-1295, 1989). Glucose-6-phosphate dehydrogenase from *Leuconostoc mesenteroides* is reported to contain a total of 38 lysine residues (Advances in Enzymology, Vol. 48, pp. 97-192, 1979; FEBS Lett. 211:2, 243-246, 1987). Under appropriate coupling conditions, the ϵ-amino groups from these lysine moieties can be modified readily. Therefore multiple molecules of an analyte (or hapten) and/or a plurality of analytes (or haptens) can be conjugated to each molecule of G6PDH.

In one embodiment of the invention, all the analytes to be determined are conjugated with a single molecule of G6PDH (a Multiple-Analytes Conjugate, or Multi-analyte Conjugate). Alternatively, a plurality of Single-Analyte Conjugates (Conjugate with only one kind of analyte) is used in the analysis. A combination of the two types of conjugates, such as one or more of Multi-analyte Conjugates mixed or supplemented with Single-Analyte Conjugates, can also be used.

Some of the analytes whose presence is sought to be determined using the methods of this invention are capable of reacting directly to G6PDH, and of generating antibodies per se. Others are not capable of covalent binding directly. Such analytes are rendered capable of covalently binding to the G6PDH by joining to them a linking group (i.e, definition of haptens) that can covalently bind to a group on the enzyme (for instance, to an amino, hydroxyl, carboxyl or mercapto group). Such linking groups may comprise, for instance, amino acids having one or more free amino or free hydroxyl groups, or may comprise carbonyl, thiocarbonyl, or carboxyl groups, or compounds containing such groups. Linking groups commonly used for this purpose include N-hydroxysuccinimide and other succinimide or maleimide-containing moieties, and 1-(3-dimethylpropyl)-3-ethylcarbodiimide. A detailed discussion of such linking groups is found in U.S. Pat. No. 3,817,837.

For example, linking groups usable in preparing conjugates for this invention include bifunctional crosslinking or coupling agents, i.e., molecules containing two reactive groups or "ends", which may be tethered by a spacer. The reactive ends can be any of a variety of functionalities including, but not limited to: amino reacting ends such as N-hydroxysuccinimide (NHS) active esters, imidoesters, aldehydes, epoxides, sulfonyl halides, isocyanate, isothiocyanate, and nitroaryl halides; and thiol reacting ends such as pyridyl disulfides, maleimides, and thiophthalimides. The heterobifunctional crosslinking reagents have two different reactive ends, e.g., an amino-reactive end and a thiol-reactive end, while homobifunctional reagents that are usable in preparing the conjugates of this invention have two similar reactive ends. Examples of such include bismaleimidohexane (BMH) which permits the cross-linking of sulfhydryl-containing compounds, and NHS homobifunctional crosslinkers such as disuccinimidyl suberate (DSS) as well as the water soluble analogs, sulfo-NHS esters.

Some other suitable linking groups for use in the present invention include, but are not limited to, maleimido-NHS active esters coupling agents such as m-maleimidobenzoyl-N-hydroxy-succinimide ester (MBS); succinimidyl 4-(N-maleimidomethyl)cyclohexane-1-carboxylate (SMCC); succinimidyl 4-(p-maleimidophenyl)butyrate (SMPB) and derivatives thereof, including sulfosuccinimidyl derivatives such as sulfosuccinimidyl 4-(N-maleimido-methyl) cyclohexane-1-carboxylate (sulfo-SMCC); m-maleimidobenzoyl-sulfosuccinimide ester (sulfo-MBS) and sulfosuccinimidyl 4-(p-maleimidophenyl)butyrate (sulfo-SMPB) (Pierce). Other suitable heterobifunctional reagents include commercially available active halogen-NHS active esters coupling agents such as N-succinimidyl bromoacetate and
N-succinimidyl(4-iodoacetyl)aminobenzoate (SIAB) and the sulfosuccinimidyl derivatives such as sulfosuccinimidyl (4-iodoacetyl)aminobenzoate (sulfo-SIAB) (Pierce). Another group of coupling agents is the heterobifunctional and thiol cleavable agents such as N-succinimidyl 3-(2-pyridyidithio)propionate (SPDP) (Pierce).

Other commercially available homobifunctional crosslinking reagents include, but are not limited to, the imidoesters such as dimethyl adipimidate dihydrochloride (DMA); dimethyl pimelimidate dihydrochloride (DMP); and dimethyl suberimidate dihydrochloride (DMS).

The choice of the amine-reactive modification reagent, thiol introducing agent or other activating agent is not critical, but one skilled in the art will know of suitable or preferred agents for use with the particular analyte whose presence in the sample is to be determined. Therefore, the linking group to be used will generally be determined empirically.

The conjugates are prepared by contacting the activated analyte or hapten with a buffered solution of G6PDH under typical conditions for formation of such conjugates. Typical conditions for forming such conjugates include a temperature of from about 2° C. to about 25° C., a pH of from about 5 to about 10, and a contact time of from less than an hour to several days. The ratio of analyte to G6PDH is generally dependent on the desirable % of deactivation and % inhibition the resulting conjugate exhibited upon binding to specific antibody or receptor.

The G6PDH-analyte binding pair member conjugates are mixed with receptors that are specifically reactive to both the conjugates and the free analytes. The receptors can be any composition that can bind effectively and specifically to the analytes and when bound to the conjugates effect an inhibition of the enzyme G6PDH. Antibodies are the most convenient receptors but other receptors would include soluble forms of natural receptors to ligand/analytes such as lectins (for carbohydrates), opioid receptors (for morphine and opioid peptides), hormone binding proteins (for hormones), enzymes (for substrates, inhibitors, or cofactors), intrinsic factor (for Vitamin $B_{12}$), folate binding protein (for folic acid), farnesyltansferase (FTase) for Ras, and fibrinogen receptor (for fibronectin and related peptides), etc. The receptors can also be binding proteins that are formed by random display on phage coats or produced by genetic engineering processes.

To the extent that antibodies are preferred, we intend the term to broadly include one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology.

Thus, the term antibody, as used herein also includes antibody fragments either produced by the modification of whole antibodies or synthesized de novo using recombinant DNA methodologies. Preferred antibodies include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked VH-VL heterodimer which may be expressed from a nucleic acid including VH- and VL-encoding sequences either joined directly or joined by a peptide-encoding linker(Euston, et al. (1988) Proc. Nat. Acad. Sci. USA, 85: 5879-5883.) While the VH and VL are connected to each as a single polypeptide chain, the VH and VL domains associate non-covalently. The first functional antibody molecules to be expressed on the surface of filamentous phage were single-chain Fv's (scFv), however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to g3p (see, e.g., U.S. Pat. No: 5733743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778).

Particularly preferred antibodies include all those that have been displayed on phage (e.g., scFv, Fv, Fab and disulfide linked Fv (Reiter et al. (1995) Protein Eng. 8: 1323-1331). Antibodies can also include diantibodies, miniantibodies, or chimeric antibodies.

Among the analytes drugs whose presence may be determined using this invention include, but not limited to, opium, the opioid analgesics, various alkaloids, catecholamines, epinephrine, amphetamines, barbiturates, tetrahydrocannabinol (THC)—the active ingredient in marijuana, cocaine, phencyclidine (PCP), 3,4-methylendioxymethamphetamine (MDMA, or ecstasy) and its related compounds such as 3,4-methylendioxyamphetamine (MDA) and 3,4-methylenedioxyethylamphetamine (MDEA), ketamine, lysergic acid diethylamind (LSD), , γ-hydroxybutyrate (GHB), tranquilizers, amino acids, sugars, peptides, nucleic acids, nucleosides, nucleotides, antibiotics, hormones, steroids, bacterial or microbial antigens or toxins, chemical and biological warfare agents, and industrial chemicals, etc. Included in these classes are analogs, metabolites, and derivatives of such compounds.

The class of opioid analgesics includes morphine, heroin, codeine, hydromorphone, fentanyl, oxycodone, buprenorphine, butorphanol, nalbuphine, methadone, dextromoramide, dipipanone, phenadoxone, propoxyphene (Darvon®), and acetylmethadol. Other alkaloids that can be detected using this invention include the steroid alkaloids, the iminazolyl alkaloids, the isoquinoline alkaloids, the quinoline alkaloids (including quinine), and the diterpene alkaloids. Catecholamines include cotarnine, narceine, noseapine and papaverine epinephrine, L-dopa, and ephedrine. Amphetamines and related compounds include amphetamine, methamphetamine, and the like. Barbiturates include veronal, pentobarbital, amobarbital, secobarbital, phenobarbital, and thiopental, etc. Mono-, di-, and poly-carbohydrates (or peptides, or nucleosides, or nucleotides), Vitamins and diet supplements such as folic acid, Vitamine $B_{12}$, biotin, Vitamin A, and Vitamin E, Tranquilizers such as meprobamate, benzodiazepines, and tricyclic anti-depressants are also compounds of interests.

Amino acids whose presence may be detected include glycine, alanine, serine, histidine, and methionine, etc. Antibiotics such as gentamycin, tobromycin, and vancomycin, etc. Microbial antigens such as *Clostridium difficile* antigen, Toxin A, and aflatoxin $B_1$, etc. Hormones, such as Thyroid hormones ($T_3$ and $T_4$). Steroids include various estrogens and androgens such as ethynylestradiol, testosterone and androsterone, etc. Chemical and biological warfare agents such as mustard gas, Sarin, Tabun, *Bacillus anthracis* (Anthrax) antigens, and Smallpox viral antigens, etc., can form panel of assays for valuable purposes. And industrial chemicals include flavoring agents, food additives, preservatives, food contaminants, air and chemical pollutants, pesticides, and herbicides, etc. Additional applications would include the high throughput screening of potential pharmaceutical agents against various infectious organisms or functional receptors, and vise versa.

The invention may also be used to determine the presence in a sample of metabolites, derivatives and analogs of the above.

The sample to be tested for the presence of the analytes is contacted with the conjugate or conjugates thus prepared, antibody/receptor, and substrate(s), and a homogeneous competitive enzyme immunoassay is carried out.

In general, the assay is of the type known as an Enzyme-Multiplied Immunoassay Technique (EMIT), which uses an enzyme-ligand conjugate. In the present invention this assay can use: (a) one or more conjugates from the enzyme G6PDH and a plurality of analytes (Multi-analyte Conjugate), (b) a plurality of conjugates from individual analyte and G6PDH (Single-Analyte Conjugate), (c) a combination of (a) and (b).

The assay is based on competition between the analyte-enzyme conjugate(s) and the free analyte(s) in the sample for a fixed amount of specific antibody(ies). Enzyme activity decreases upon binding to the antibody, and the analyte concentration in the sample is measured in terms of enzyme activity. Active enzyme converts nicotinamide adenine dinucleotide (NAD) to NADH, resulting in an absorbance change that can be measured spectrophotometrically at 340 nm.

In the absence of free analyte(s) in the sample, the specific antibody(ies) binds to the analyte-enzyme conjugate(s) causing a decrease in enzyme activity. On the other hand, when free analyte(s) is(are) present in the sample, antibody(ies) would bind to the free analyte(s), the unbound analyte-enzyme conjugate(s) then exhibits the maximal enzyme activity.

To carry out the process of this invention, the concentrations of the antibody(ies) and analyte-enzyme conjugate(s) in the system are adjusted so that the enzyme activity at the cutoff level of each analyte is the same or at close proximity for all analytes whose presence in the sample is sought to be detected. These enzyme rates are within 5% of each other, preferably within 4%, and more preferably, within 3% of each other.

The extent of deactivation of the G6PDH due to conjugation with analyte(s) and the inhibition of the deactivated due to competitive binding with antibodies determined by conventional procedures as described in the EMIT literatures and the U.S. Pat. No. 3,817,837.

In testing samples to determine the presence of suspected analytes according to the invention, the G6PDH is deactivated by from about 20 to about 85%, preferably from about 20 to about 60%, and the deactivated enzyme is then inhibited by from about 20 to about 85% when testing with an excess of individual antibody/receptor solutions or mixture of antibodies/receptors; preferably from about 40 to about 80% when testing with an excess of individual antibody/receptor solutions or mixture of antibodies/receptors.

The following is a generic procedure for setting up reagents for simultaneously detection of multiple analytes as described in the present invention. Using a plurality of single-analyte-G6PDH conjugates, one works out the conditions for appropriate concentrations required on antibody (Ab) and G6PDH conjugate for each individual assay first. When preparing for a 2-in-1 assay, you select the assay conditions where the Δ rate (the difference in the enzyme rate) between the negative calibrator and the cutoff calibrator is equivalent for each individual assay. Then you prepare a mixed-Ab solution and a mixed-G6PDH conjugates solution for the 2-in-1 assay according to concentrations for the individual assay. One then finishes by making final adjustments on the concentrations of Ab and C6PDH conjugate solutions to ensure the equivalent rate at cutoff for each analyte is achieved in the assay.

The same process is used to create reagents for a 3-in-1 assay. First you work out the 2-in-1 assay formulations, and then determine the final Δ rate between the negative calibrator and cutoff calibrator of the 2-in-1 assay. Next you select a condition for the third analyte assay (individual assay) where its Δ rate between negative calibrator and its cutoff calibrator is equivalent to that of the 2-in-1 assay. Then, calculate and spike appropriate amounts of Ab and G6PDH conjugate of the $3^{rd}$ analyte into the corresponding reagents in the 2-in-1 assay. (The dilution effect caused by spiking the $3_{rd}$ component should be minimal since the stock solution of Ab or G6PDH conjugate is typically more than 100 fold in concentration comparing to the assay reagent solutions). One then fine-tunes the Ab and G6PDH conjugate components in the mixed solutions so that a uniform (or equivalent) enzyme rate for the cutoff of each analyte is achieved in the assay. This basic approach can be scaled to address a n-in-1 assay.

When using multiple-analytes-G6PDH conjugate the same basic approach is followed except multiple-analytes-G6PDH conjugates are prepared so that the % inhibitions of the resulting deactivated G6PDH are equivalent for each corresponding analyte in the current assay as in the assay using a plurality of single-analyte-conjugates.

Both mixture of single-analyte-G6PDH conjugate(s) and multiple-analytes- conjugate(s) can be used in this invention. As the number of analytes (n) in the assay gets bigger, the preparation of one G6PDH conjugate with all analytes on it becomes harder. However, an assay can be accomplished by using the imperfect multiple-analytes-G6PDH supplementing with single-analyte-conjugates. It can also be set up with one or more multiple-analytes-G6PDH conjugates each with lower numbers (m<n) analytes on each enzyme and supplementing with single-analyte conjugate(s) when necessary.

Kits for conducting enzyme immunoassays form another aspect of the invention. In addition to typical components of immunoassay kits such as antibodies, substrates, buffers and other solutions, calibrators or standards and the like, such kits will contain one or more conjugates of G6PDH with analytes whose presence is sought. As described above, these conjugates may comprise a single Multi-analyte Conjugate, a mixture of Single-Analyte Conjugates, combination of a Multi-analyte Conjugate and as many Single-Analyte Conjugate(s) as necessary, a plurality of Multi-analyte Conjugates, or any combination of the above. The embodiment of the conjugates that is preferred for use in a given situation will be determined empirically.

In general, using the process of this invention, up to 4, preferably up to 6 or higher number of analytes can be readily detected. It will be convenient to provide a kit that can be used to search simultaneously for the presence (above the predetermined concentration or cutoff level) of a group of analytes that would normally be checked individually for the same sample. For instance, a kit for blood testing of rehabilitated drug addicts or probational criminals can be assembled that would include conjugates of common drugs of abuse, such as THC/marijuana, morphine or heroin, PCP, amphetamines, methadone, propoxyphene, and cocaine, etc. One or more kits for testing hospital patients for drug use, licit or illicit, can similarly be prepared. One kit for instance may contain conjugates for commonly used illicit drugs for pre-employment drug-screening which typically include the so-called NIDA-5 (The National Institute on Drugs of Abuse) panel: opiate, cocaine, THC/marijuana, PCP, and amphetamines (include both amphetamine and methamphetamine). Another kit may include conjugates for licit drugs that may commonly be taken in excess or whose presence need be ascertained in order to properly treat patients. Such a kit may include, for instance, conjugates directed to barbiturates, salicylate, tricyclic antidepressants such as imipramine, desipramine, amitriptyline, and nortriptyline, etc. An industrial kit for testing prospective employees could contain conjugates directed to alcohol, diuretics, cardiovascular drugs, and the like. A kit for testing for exposure to industrial chemicals could be prepared containing common hazardous chemicals, or chemicals relevant to a particular site or occupation. Such kits may contain conjugates directed to certain solvents, chemical intermediates, expected products, and the like. Similarly, kits used to monitor workers or others for exposure to pesticides may be prepared, with conjugates directed to the type of pesticides, or specific pesticides, in question.

A kit for testing the presence of any chemical or biological warfare agents, such as the nerve agents (e.g., Sarin, Tabun, and Soman, etc.), mustard gas, Staphylococcus B Enterotoxin, Botulinum Toxin, Anthrax antigen(s), and smallpox antigen(s), etc. can be very useful. The application can also be extended for kits that can be used in the high throughput screening of potential pharmaceutical agents against various infectious agents, and/or against various functional proteins or receptors, etc., and vise versa.

It should be noted that the processes and kits of this invention are intended for the use of screening, that is, determining whether one or more of a plurality of target analytes is present in the sample in question, at a concentration at or above some predetermined minimum or maximum level (Cutoff). The invention is not aimed at determining the exact amount of analyte actually present in such a sample. Such a determination would normally be done, subsequent to screening using this invention, using typical methods available for that purpose, for those analytes where quantification of such analyte(s) is desired. This invention enables quick screening for multiple analytes in a single test, as opposed to previously required conducting of individual screens for each of the analytes.

In a preferred method of operation, the extent of inhibition of the activity of the G6PDH simply indicates whether any of the analytes whose presence above a predetermined level is sought, is in fact present at above that level. A positive result does not distinguish which, or how many analytes, nor how much of each of these analytes, is present in the sample. That can be determined subsequently, in tests for the presence and quantity of individual analytes indicated in this screen. On the other hand, a negative result indicates that none of the screened analytes are present. The time and cost-saving can be enormous with the availability of such a screen method described in the present invention.

The invention is further illustrated by the following examples, which are only illustrative and are not intended to limit the definition of the invention in any way.

EXAMPLE 1

A General Procedure for Preparation of Enzyme Solution for Conjugation

Glucose-6-phosphate dehydrogenase (G6PDH) in ammonium sulfate suspension was dialyzed against 50 mM Tris buffer, pH 8.3 to remove all ammonium sulfate. The resulting solution was then adjusted to a final concentration of 4.0-8.0 mg/mL.

EXAMPLE 2

A General Procedure for Activation of Analyte or Hapten for Conjugation with the Amino Function of the Enzyme G6PDH Analyte or hapten of proper structure containing a carboxylic group can be activated with N-hydroxysuccinimide (NHS) and 1-(3-dimethylpropyl)-3-ethylcarbodiimide (EDAC) in anhydrous DMF as illustrated in the following example (Example 3) and in the U.S. Pat. Nos. 3,817,837 and 5,328,828.

EXAMPLE 3

Activation of O-Carboxymethyloxime of Phencyclidine (PCP)

Stepwise preparation of a PCP hapten such as 1-(1-phenyl-4-(O-carboxylmethyloximocyclohexyl) piperidine (Abbr. as the O-Carboxymethyloxime of PCP) can be found in U.S. Pat. No. 4,446,065. The _PCP-acid (18.3 mg, $5.0 \times 10^{-2}$ mmole), NHS (7.5 mg, $6.5 \times 10^{-2}$ mmole) and EDAC (12.8 mg, $6.5 \times 10^{-2}$ mmole) were mixed in a 5 ml flask. The flask was connected to a vacuum for 30 minutes and 2 ml of DMF (dried and distilled over $CaH_2$) was then added under an argon atmosphere in the cold room temperature. The solution was allowed to stir overnight.

Other common functional groups that readily reactive with amino group include sulfydryl (—SH) and isothiocyanate (—N=C=S). p-Isothiocyanatobenzoylecgonine (a hapten for cocaine metabolite) can directly react with the enzyme solution without further activation. d, 1-m-(Mercaptoethylamidomethoxy)amphetamine and d, 1-m-(Mercaptoethylamidomethoxy)methamphetamine are sulfhydryl-containing haptens for amphetamine and methamphetmine, respectively, that required no further activation for conjugation with the enzyme. Preparation of such haptens can be found in the literature and in the U.S. Pat. Nos. 3,817,837 and 5,328,828.

Enzyme-analyte conjugate is then prepared by reacting the activated hapten with the enzyme. The conjugation of the NHS-activated O-Carboxylmethyloxime of PCP to G6PDH described below illustrates a general procedure for preparation of a Single-Analyte Conjugate.

EXAMPLE 4

Preparation of PCP-G6PDH (PCP-Ez or P-Ez) Conjugate

To 2 mL of the above describe G6PDH in Tris, pH 8.3, solution (4.3 mg/mL) in 4° C. was first added 100 mg of disodium glucose-6-phosphate with stirring. The activated hapten described in the Example 1 was then transferred to a syringe pump, and slowly added to the enzyme solution. The addition rate was set at 45 µl/hr. Aliquots of the reaction mixture were periodically withdrawn to determine the extent of enzyme deactivation (%D) as well as the inhibitability (%I) of the conjugate with anti-PCP antibody. The antibody was added in excess to the amount of analyte added.

Reagents required and the assay procedure for monitoring enzyme deactivation and inhibition are described in the following:

| Conjugate Diluent: | |
| --- | --- |
| Tris | 200 mM |
| NaCl | 90 mM |
| BSA | 1.0% |
| Triton X-100 | 0.01% |
| Sodium Azide | 0.09% |
| pH | 8.2 |
| Antibody/Substrate Diluent: | |
| Tris | 20 mM |
| Disodiuni Glucose-6-Phosphate | 6.6 mM |
| NAD | 4.0 mM |
| NaCl | 90 mM |
| BSA | 1.0% |
| Sodium Azide | 0.09% |
| pH | 5.0 |

Assay procedure: All rate measurement experiments were carried out in duplicates.

1. Dilute an aliquote (2 uL) of the starting enzyme solution with conjugate diluent to 2 mL, and from which take 50 uL and further dilute to 1 mL (20,000× dilution)
2. Dilute the specific antibody solution to an appropriate concentration, typically 20-40 ug/mL, with the antibody diluent
3. Take 75 uL of the diluted enzyme solution from step 1 mixed with 175 uL of antibody solution from step 2 onto a well of microtiter plate (or a strip), and the enzyme kinetic is measured for 1 minute with Biotek EL808 Ultra Microplate Reader. This is the reference rate for the enzyme.
4. Dilute an aliquot of the in-progress enzyme conjugation solution 20000× as described in step 1
5. Take 75 uL of the diluted enzyme conjugate solution from step 4 into a well on a microtiter plate (or a strip) and 75 uL of the starting enzyme solution from step 1 into another well.
6. To each well is then added 175 uL each of the diluted antibody solution from step 2, and the enzyme kinetic is measured for 1 minute on Biotek as described below.
7. Comparing the rate of the starting enzyme solution with the in-process enzyme conjugate solution to determine the % deactivation.

8. Pipette 2 of 75 uL of the in-process, diluted enzyme conjugation solution from step 4 into 2 separate wells on a microtiter plate (or a strip)
9. To one well is added 175 ul of the antibody diluent (without antibody), and to another is added 175 uL of the diluted antibody solution from step 2. The enzyme rate of the two mixtures are measured for 1 minute on Biotek.
10. Comparing the enzyme rate of the in-process enzyme conjugate with and without antibody to determine the % inhibition of the conjugate.

The measurement on Biotek is accomplished under the following conditions: A first reading of optical density (OD) at 340 nm was taken after 20-second incubation and continue monitored for additional 60 seconds in 20 second intervals. The kinetics was then calculated and expressed in $\Delta mA/min$.

The in-process PCP-Ez gave the following %D and %I results:

| Total hapten added (μl) | % D | % I |
|---|---|---|
| 100 | 27 | 40 |
| 130 | 37 | 66 |
| 140 | 46 | 70 |

The conjugation reaction was terminated at 70% deactivation, and the resulting crude conjugate was purified by a SEPHADEX®-G50 column with 50 mM Tris buffer, pH 8.0. To the purified PCP-G6PDH conjugate was then added bovine serum albumin to 0.1% and sodium azide to 0.05% (with a solution of 10% BSA in 5% sodium azide) for storage.

Preparation of a Multi-analyte Enzyme Conjugate followed the same process for enzyme preparation and analyte or hapten activation. The conjugation process, however, may be accomplished in several different ways. The following examples (Examples 5, 6, and 7) illustrated some of the different approaches taken.

EXAMPLE 5

Preparation of Amphetamine-Methamphetamine-G6PDH Conjugate (Amp-Mamp-Ez, a Two-Analytes Enzyme Conjugate)

Amphetamine hapten (12 mg), methamphetamine hapten (15 mg), NHS (25 mg), and EDAC (50 mg) were weighed into a small flask. The solid mixture was dried under a vacuum at 45° C. for 3 hours before addition of 2 mL of anhydrous DMF. The solution was then stirred at 4° C. overnight.

A G6PDH solution (8 ml) was prepared as described above. The activated mixed-hapten solution in a 1-ml syringe was transferred to a syringe pump and slowly added to the enzyme solution at a rate of 50 μl/hr. The conjugation was monitored as described before. Inhibition was checked by amphetamine antibody ("by anti-A") and by methamphetamine antibody ("by Anti-M"). The following results were observed for a typical conjugation;

| Total hapten added (μl) | % D | % I (by Anti-A) | % I (by Anti-M) |
|---|---|---|---|
| 150 | 12 | 29 | 34 |
| 200 | 20 | 40 | 45 |
| 300 | 35 | 50 | 55 |
| 500 | 46 | 66 | 68 |
| 700 | 55 | 73 | 75 |

The conjugation was then terminated and the two-analyte (amphetamine & methamphetamine) enzyme conjugate was purified with a SEPHADEX®G-50 column, and stored in the same way as described for the single analyte conjugate.

EXAMPLE 6

Preparation of Methamphetamine-Opiate-Phencyclidine-G6PDH Conjugate ("MOP-Ez", a Three-Analyte Enzyme Conjugate) by "Simultaneous Addition" of Haptens:

To a Tris buffered solution of G6PDH (20 mg in 4 mL) was added 300 mg of disodium G6P. The solution was stirred at ice-bath temperature for 30 minutes and equally divided into 4 portions. Three aliquots were used for individual analyte conjugation (3 Single-Analyte Enzyme Conjugates) and the $4^{th}$ aliquot for a Multiple Analyte Conjugation (the Three-Analyte Enzyme Conjugate).

Hapten Activation: A methamphetamine hapten (12.3 mg), NHS (7 mg), and EDCI (11.5 mg) were dissolved in 1 ml of anhydrous DMF. The solution was stirred at 4° C. overnight. Separately, an opiate hapten (19.1 mg), NHS (7 mg), and EDCI (11.5 mg) were dissolved in 1 ml of anhydrous DMF and a phencyclidine hapten (18.3 mg), NHS (7 mg) and EDCI (11.5 mg) were dissolved in 1 ml of anhydrous DMF in separate flasks. The solutions were similarly stirred in the cold room overnight. A 200 uL aliquot was then taken from each flask and pooled into a new container.

Preparation of MOP-Ez Conjugate: The three individually activated hapten solutions and the pooled activated hapten mixture were separately added to the four enzyme aliquots at the rate of 10 ul at a time (The Single-Analyte Conjugates were prepared for supplementary purpose as described in Example 13) Reactions were allowed to proceed for an hour in-between each addition of hapten solution. At the end of each interval, the enzyme activity from each conjugation was monitored. The summary of % deactivation from the mixed-analyte conjugation and the three individual conjugations were tabulated:

| Total hapten added (μl) | MOP-Ez % D | M-Ez % D | O-Ez % D | P-Ez % D |
|---|---|---|---|---|
| 10 | 21 | 24 | 22 | 27 |
| 20 | 39 | 40 | 30 | 47 |
| 30 | 49 | 54 | 42 | 60 |
| 40 | 63 | 55 | 50 | 60 |

All conjugation reactions were terminated at 40 uL of activated hapten solution addition, and the % inhibitions of each Single-Analyte Conjugate was evaluated with its specific antibody, and the results were 72% I for M-Ez, 50% I for O-Ez, and 57% I for P-Ez. The % inhibition of the Multi-analyte Conjugate, MOP-Ez, was tested with either an excess individual antibody solutions or with an excess of the mixed antibodies:

| By Anti-M | by Anti-O | by Anti-P | by Mixed antibodies |
|---|---|---|---|
| 32% | 35% | 26% | 60% |

EXAMPLE 7

Preparation of Methamphetamine-Opiate-Phencyclidine-G6PDH (MOP-Ez) Conjugate by "Sequential Addition" of Haptens:

To G6PDH enzyme (8 mg) in 2 ml of 50 mM Tris buffer was added 150 mg of disodium glucose-6-phosphate. The conjugation was carried out with activated phencyclidine hapten described in Example 4 first, followed by opiate; and finished with methamphetamine. No purification was carried out in-between hapten switch. The final conjugate was then purified and worked up as described before.

The following results were observed:

|  | Volume added | % D | overall % D |  |
|---|---|---|---|---|
| Phencyclidine hapten: | 10 uL | 14 | 14 |  |
|  | 20 | 23 | 23 |  |
|  | 30 | 39 | 39 |  |
|  | 40 | 43 | 43 |  |

|  |  |  | overall % D | |
|---|---|---|---|---|
| Opiate hapten: | Volume added | % D | Theo. | Observ. |
|  | 0 | 0 | (43) | 43 |
|  | 15 | 32 | (–>60) | 50 |
|  | 30 | 38 | (–>65) | 54 |
|  | 45 | 47 | (–>70) | 60 |
| Methamphetamine hapten: | 0 | 0 |  | 60 |
|  | 15 | 30 | (–>79) | 64 |
|  | 30 | 43 | (–>83) | 78 |
|  | 40 | 50 | (–>85) | 81 |

The MOP-Ez prepared by the sequential addition of activated hapten procedure gave the following % inhibition profile:

| by Anti-M | by Anti-O | by Anti-P | by Mixed antibodies |
|---|---|---|---|
| 57% I | 23% | 32% | 71% |

Example 8 illustrated the basic EMIT assay method and of using the Single-Analyte conjugate in the EMIT assay. Examples 9-13 illustrated the novel technique disclosed in the current invention: Utilize a Multiple-Analyte conjugate, or a mixture of Single-Analyte conjugate, or a mixture of Multiple-Analyte Conjugate(s) supplementing with Single-Analyte conjugate(s) to carry out the screening process when the presence of one of more analytes is sought in a single screening assay.

EXAMPLE 8

Typical EMIT Assay Method:

Calibrators:

Calibrator sets containing d-amphetamine, d-methamphetamine, morphine (an opiate), and phencyclidine were prepared by spiking the drugs into a BSA-containing phosphate buffer, pH 7.0. The concentrations of the d-amphetamine and d-methamphetamine calibrator sets were 0, 1000, and 2000 ng/mL. The concentrations of the opiate calibrators were 0, 300, and 1000 ng/mL. The concentrations of phencyclidine calibrator were 0, 25, and 100 ng/mL. For convenience the three levels of calibrator were designated as Negative, Cutoff, and High Calibrators.

| Antibody/Substrate Diluent: | |
|---|---|
| Tris | 20 mM |
| Disodium G6P | 6.0 mM |
| NAD | 5.0 mM |
| NaCl | 0.5% |
| BSA | 0.1% |
| Sodium Azide | 0.09% |
| pH | 5.4 |

Antibody/Substrate reagent ($R_1$) was prepared by diluting specific monoclonal antibodies to phencyclidine, opiate, amphetamine, and methamphetamine, respectively, into the antibody/substrate buffer. The finally antibody concentration in each assay can only be determined experimentally. In general, it required $4 \times 10^{-9}$ to $2 \times 10^{-7}$ M depending on the antibody affinity, the assay range, and hapten number of the enzyme conjugate. Typically individual antibody inhibited the enzyme activity of its specific enzyme conjugate approximately 30-45% within the assay range (Neg. Calibrator to High Calibrator Concentration).

| Enzyme Conjugate Diluent: | |
|---|---|
| Tris | 100 mM, |
| NaCl | 0.9%, |
| Sodium Azid | 0.09% |
| BSA | 1%, |
| pH | 8.2. |

Enzyme Conjugate Reagent ($R_2$) was prepared by diluting hapten(s)-labeled enzyme conjugate(s) in the enzyme-conjugate diluent to a concentration that would result in a maximum rate of about 500-1000 mA per minute as measured at 37° C. according to the assay method described below. The concentration of the analyte-enzyme is determined experimentally. In general, they are from $1 \times 10^{-9}$-$4 \times 10^{-8}$ M depending on the antibodies used, assay range required, and the cutoff level of the analyte. Initial analysis assay is conducted with a Biotek plate reader and then automated in an open chemical analyzer system such as a Cobas Mira, Hitachi 717 or Synchron X4CE.

The enzyme rate of the cutoff calibrator is used as reference for distinguishing positive from negative samples. A sample with a change in absorbance ($\Delta mA/min$) equals to or greater than that obtained with the cutoff calibrator is considered positive. A sample with a change in absorbance value lower than that obtained with the cutoff calibrator is considered negative.

Assay Protocol:

Fifteen microliters (15 µl) of calibrator (or sample) was incubated with 175 µl of the antibody/substrate reagent ($R_1$) for 200 seconds at 37° C., followed by addition of 75 µl of the enzyme conjugate reagent ($R_2$). The enzyme kinetic at 340 nm was measured with a Biotek microtiter plate reader under the parameters described before.

Using the above procedure, an amphetamine-G6PDH (Amp-Ez), and a methamphetamine-G6PDH (Mamp-Ez) were prepared. The EMIT performance of these conjugates were performed, and typical 3 points calibration curves for a specific amphetamine assay and a specific methamphetamine assay were obtained as follows:

| Calibrator | ΔmA/min (Amp-Ez) | ΔmA/min (Mamp-Ez) |
|---|---|---|
| Neg. | 138 | 135 |
| Amp or Mamp Cut-off | 316 | 291 |
| Amp or Mamp High | 370 | 335 |

EXAMPLE 9

EMIT Assay with an Amphetamine-Methamphetamine-Enzyme Conjugate (Amp-Mamp-Ez): AM 2-in-1 Assay The Amp-Mamp-Ez ($4.7 \times 10^{-9}$ M) prepared as described previously (Example 5) was tested with a mixture of amphetamine and methamphetamine antibodies at appropriate concentrations ([anti-M]: $2.2 \times 10^{-8}$ M, [anti-A]: $3.1 \times 10^{-8}$ M) using amphetamine or methamphetamine calibrators as samples:

| Calibrator | AM 2-in-1 Assay Rate (mA/min) | Calibrator | AM 2-in-1 Assay Rate (mA/min) |
|---|---|---|---|
| Neg. | 227 | Neg. | 227 |
| Amp 1000 | 339 | Mamp 1000 | 335 |
| Amp 2000 | 414 | Mamp 2000 | 391 |

The performance of the assay was equivalent or better than that disclosed in the U.S. Pat. No. 5,328,828, and the commercially amphetamines assay kit based on the patented technique (EMIT® II Monoclonal Amphetamine/Methamphetamine Assay package insert by Syva/Behring) using a mixture of amphetamine-G6PDH and methamphetamine-G6PDH conjugates, and a pair of antibodies.

EXAMPLE 10

Methamphetamine-Amphetamine-Cocaine 3-in-1 Assay (MAC Assay with a Mixture of M-Ez, A-Ez, and C-Ez Conjugates)

In addition to the Amp-Ez and Mamp-Ez conjugate, a benzoylecgonine-Ez (Coc-Ez) was also prepared as described before. A mixture of these three Single analyte conjugates (M-Ez+A-Ez+C-Ez) was made in proper dilutions from their respective stocks (M-Ez, $4.0 \times 10^{-9}$ M; A-Ez, $5.8 \times 10^{-9}$ M, and C-Ez, $2.0 \times 10^{-8}$ M), so was a mixture of three antibodies (anti-Mamp, $3.8 \times 10^{-8}$ M; anti-Amp, $5.8 \times 10^{-8}$ M and anti-Coc, $8.0 \times 10^{-8}$ M). The calibrators concentrations for either amphetamine are 0, 1000, and 2000 ng/mL, and for benzoylecgonine they are 0, 300, and 3000 ng/mL, respectively for the negative, cutoff and high levels.

The 3-in-1 MAC assay was carried out on the Hitach 717 analyzer. The reference rates with respect to individual analyte were shown as follows:

| Cal | Mamp | Amp | Coc |
|---|---|---|---|
| Neg. | 310 | 310 | 310 |
| Cutoff | 399 | 399 | 395 |
| High | 438 | 451 | 514 |

Twenty eight (28) patient samples were evaluated by individual assays and the MAC assay reagents. The results were compared:

| Sample origin | Amphetamines* Assay | Cocaine Assay | MAC Assay +/– (rate) |
|---|---|---|---|
| 1 Healthy Donor #1 | – | – | – (321) |
| 2 Healthy Donor #2 | – | – | – (321) |
| 3 PCP positive #1 | – | – | – (323) |
| 4 PCP positive #2 | – | – | – (324) |
| 5 Methadone Positive #1 | – | – | – (326) |
| 6 Methadone Positive #2 | – | – | – (332) |
| 7 Opiate Positive #1 (also Amphetamines positive) | + | – | + (403) |
| 8 Opiate Positive Sample #2 | – | – | – (327) |
| 9 Cocaine Positive #1 | – | + | + (545) |
| 10 Cocaine Positive #2 | – | + | + (496) |
| 11 Cocaine Positive #3 | – | + | + (521) |
| 12 Cocaine Positive #4 | – | + | + (468) |
| 13 Cocaine Positive #5 | – | + | + (540) |
| 14 Cocaine Positive #6 | – | + | + (435) |
| 15 Cocaine Positive #7 | – | + | + (477) |
| 16 Cocaine Positive #8 | – | + | + (450) |
| 17 Cocaine Positive #9 | – | + | + (436) |
| 18 Cocaine Positive #10 | – | + | + (511) |
| 19 Amphetamines Positive #1 | + | – | + (440) |
| 20 Amphetamines Positive #2 | + | – | + (624) |
| 21 Amphetamines Positive #3 | + | – | + (414) |
| 22 Amphetamines Positive #4 | + | – | + (769) |
| 23 Amphetamines Positive #5 | + | – | + (454) |
| 24 Amphetamines Positive #6 | + | – | + (414) |
| 25 Amphetamines Positive #7 | + | – | + (782) |
| 26 Amphetamines Positive #8 | + | – | + (444) |
| 27 Amphetamines Positive #9 | + | – | + (408) |
| 28 Amphetamines Positive #10 | + | – | + (671) |

*Amphetamines assay determines the presence of amphetamine and/or methamphetamine.

EXAMPLE 11

Methamphetamine-Opiate-PCP 3-in-1 Assay (MOP-Ez Conjugate)

The enzyme immunoassay was performed with the Methamphetamine-Opiate-PCP-G6PDH (MOP-Ez, the 3-analyte Conjugate), prepared as described in the Example 6, and the three antibodies together. Each antibody was titrated carefully so that the enzyme rate of the assay for each drug at its cutoff calibrator concentration (for Mamphetamine, it is 1000 ng/mL, for Opiate, 300 ng/mL, and PCP, 25 ng/mL) is similar. The performance of the assay was shown in the following table:

| Calibrator | Mamp | Opiate | PCP |
|---|---|---|---|
| Negative | 286 | 286 | 286 |
| Cutoff | 345 | 334 | 340 |
| High | 379 | 368 | 361 |

EXAMPLE 12

Methamphetamine-Amphetamine-Cocaine-Propoxyphene 4-in-1 Assay (MACPx Assay with a Mixture of M-Ez, A-Ez, and Px-Ez Conjugates)

Four Single-Analyte Conjugates, M-Ez, A-Ez, C-Ez, and Px-Ez were prepared as described before. A mixture of these four conjugates was prepared, so was a mixture of the four antibodies. The final concentrations of each conjugate and antibody were summarized below:

|  | Antibody (M) | Enzyme Conjugate (M) |
|---|---|---|
| Methamphetamine | $3.7 \times 10^{-8}$ | $4.0 \times 10^{-9}$ |
| Amphetamine | $5.8 \times 10^{-8}$ | $5.7 \times 10^{-9}$ |
| Cocaine | $7.8 \times 10^{-8}$ | $1.9 \times 10^{-8}$ |
| Propoxyphene | $2.2 \times 10^{-8}$ | $6.8 \times 10^{-9}$ |

The EMIT assay was carried out using individual drug calibrators, and the enzyme rates of the Negative Calibrator, the Cutoff Calibrator (1000 ng/mL for methamphetamine or amphetamine, 300 ng/mL for either cocaine or propoxyphene), and High Calibrator (3000 ng/mL for cocaine, 1000 ng/mL for propoxyphenyl) were as follows:

| Calibrator | Mamp | Amp | Coc | Propx |
|---|---|---|---|---|
| Negative | 347 | 347 | 347 | 347 |
| Cutoff | 429 | 436 | 429 | 427 |
| High | 460 | 486 | 521 | 473 |

EXAMPLE 13

PCP-Cocaine-Opiate-Mamphetamine 4-in-1 Assay (PCOM Assay with a PCOM-Ez Conjugate Supplementing with Single-Analyte Conjugates)

A 4-analyte enzyme conjugate (Phencyclidine-Cocaine-Opiate-Methamphetamine-G6PDH, or PCOM-Ez) was prepared using simultaneous addition of activated haptens as described in Example 6. The performance of the resulting PCOM-Ez conjugate was determined to be difficult to achieve the similar enzyme rate at the cutoff of various analytes. Single-Analyte conjugates were then added to supplement the PCOM-Ez so that an equivalent enzyme rate were attained at the cutoff level of each analyte of interest.

The enzyme rates of the 5-in-1 assay with each individual drug at Negative, Cutoff, and High Calibrator Concentrations were shown in the following table:

| Calibrator | PCP | COC | OPA | Mamp |
|---|---|---|---|---|
| Neg. | 630 | 630 | 630 | 630 |
| Cutoff | 698 | 703 | 697 | 701 |
| High | 771 | 756 | 748 | 738 |

EXAMPLE 14

Methamphetamine-Amphetamine-Cocaine-Propoxyphene-Opiate 5-in-1 (MACPxO) Assay with a Mixture of M-Ez, A-Ez, C-Ez, P-Ez, and O-Ez Conjugates)

To aliquots of the mixed-Ab solution and mixed-Ez-Conjugate Solution were Spiked gradually with appropriate amounts of anti-opiate antibody to the final concentration of $2.2 \times 10^{-8}$ M, and with an appropriate amount of Opiate-G6PDH (O-Ez) conjugate to the final concentration of $7.9 \times 10^{-9}$ M. The enzyme immunoassay was conducted in a usual fashion. The results with individual drug calibrators were as follows:

| Calibrator | Mamp | Amp | Coc | Propx | Opiate |
|---|---|---|---|---|---|
| Negative | 499 | 499 | 499 | 499 | 499 |
| Cutoff | 578 | 582 | 577 | 578 | 576 |
| High | 612 | 638 | 664 | 624 | 624 |

Sixty (from single drug testings) clinical samples were evaluated with the MACPxO reagents, and the results validated the concept of the 5-in-1 screening test described in the present patent disclosure: All those samples tested positive to at least one of the 5 drugs under investigation (Methamphetamine, Amphetamine, Cocaine, Propoxyphene, and Opiates) gave positive results in the 5-in-1 assay. Other samples which were "only" positive to drug(s) THC, Methadone, PCP, Benzodiazepines, and/or Barbituates, which were not intended by the current 5-in-1 assay, gave negative results. So were the negative samples in the individual assays, they were tested negative in the 5-in-1 assay.

|  | Amps (Amp & Methamp) | Coc | Opa | PCP | Md | THC | Bz | Ba | Px | MAC-PxO (rate) |
|---|---|---|---|---|---|---|---|---|---|---|
| 1 | + | − | − | − | − | − | − | − | − | +(675) |
| 2 | + | − | − | − | − | − | − | − | − | +(691) |
| 3 | + | − | − | − | − | − | − | − | − | +(618) |
| 4 | + | − | − | − | − | − | − | − | − | +(717) |
| 5 | − | − | − | − | − | − | − | − | − | −(528) |
| 6 | + | − | − | − | − | − | − | − | − | +(710) |
| 7 | − | + | − | − | − | − | − | − | − | +(651) |
| 8 | − | + | − | − | − | − | − | − | − | +(733) |
| 9 | − | + | − | − | − | − | − | − | − | +(695) |
| 10 | − | + | − | − | − | − | − | − | − | +(662) |
| 11 | − | + | − | − | − | − | − | − | − | +(672) |
| 12 | − | + | + | − | − | − | − | − | − | +(797) |
| 13 | − | + | + | − | − | − | − | − | − | +(734) |
| 14 | − | − | + | − | − | − | − | − | − | +(636) |
| 15 | − | − | + | − | − | − | − | − | − | +(701) |
| 16 | − | − | + | − | − | − | − | − | − | +(590) |
| 17 | − | − | + | − | − | − | − | − | − | +(606) |
| 18 | − | − | + | − | − | − | − | − | − | +(629) |
| 19 | − | − | + | − | − | + | − | − | − | +(593) |
| 20 | − | − | + | − | − | + | − | − | − | +(664) |
| 21 | − | − | + | − | − | − | + | + | − | +(685) |
| 22 | − | − | + | − | − | − | + | + | − | +(752) |
| 23 | − | − | − | + | − | − | − | − | − | −(501) |
| 24 | − | − | − | + | − | − | − | − | − | −(504) |
| 25 | − | − | − | + | − | − | − | − | − | −(500) |
| 26 | − | − | − | + | − | − | − | − | − | −(502) |
| 27 | − | − | − | + | − | − | − | − | − | −(492) |
| 28 | − | − | − | − | + | − | − | − | − | −(509) |
| 29 | − | − | − | − | + | − | − | − | − | −(503) |
| 30 | − | − | − | − | + | − | − | − | − | −(515) |
| 31 | − | − | − | − | + | − | − | − | − | −(513) |
| 32 | − | − | − | − | + | − | − | − | − | −(493) |
| 33 | − | − | − | − | − | + | − | − | − | −(547) |
| 34 | − | + | − | − | − | − | − | − | − | +(645) |
| 35 | − | − | − | − | − | + | − | − | − | −(516) |
| 36 | − | − | − | − | − | + | − | − | − | −(503) |
| 37 | − | − | − | − | − | + | − | − | − | −(536) |
| 38 | − | − | − | − | − | + | − | − | − | −(534) |
| 39 | − | − | − | − | − | + | − | − | − | −(510) |
| 40 | − | − | − | − | − | − | + | − | − | −(508) |
| 41 | − | − | − | − | − | − | + | − | − | −(504) |
| 42 | − | − | − | − | − | − | + | − | − | −(524) |
| 43 | − | − | − | − | − | − | + | − | − | −(506) |
| 44 | − | − | − | − | − | − | + | − | − | −(497) |
| 45 | − | − | − | − | − | − | − | + | − | −(506) |
| 46 | − | − | − | − | − | − | − | + | − | −(510) |

-continued

| | Amps (Amp & Methamp) | Coc | Opa | PCP | Md | THC | Bz | Ba | Px | MAC-PxO (rate) |
|---|---|---|---|---|---|---|---|---|---|---|
| 47 | − | − | − | − | − | − | − | + | − | −(513) |
| 48 | − | − | − | − | − | − | − | + | − | −(508) |
| 49 | − | − | − | − | − | − | − | + | − | −(531) |
| 50 | − | − | − | − | − | − | − | − | + | +(593) |
| 51 | − | − | − | − | − | − | − | − | + | +(600) |
| 52 | − | − | − | − | − | − | − | − | + | +(606) |
| 53 | − | − | − | − | − | − | − | − | + | +(603) |
| 54 | − | − | − | − | − | − | − | − | + | +(613) |
| 55 | − | − | − | − | − | − | − | − | − | −(496) |
| 56 | − | − | − | − | − | − | − | − | − | −(496) |
| 57 | − | − | − | − | − | − | − | − | − | −(502) |
| 58 | − | − | − | − | − | − | − | − | − | −(504) |
| 59 | − | − | − | − | − | − | − | − | − | −(509) |
| 60 | − | − | − | − | − | − | − | − | − | −(508) |

Abbreviations: Amps (amphetamine+methamphetamine); Coc (cocaine); Opa (opiates); PCP (phencyclidine); Md (methadone); THC (tetrahydrocannabinol); Bz (benzodiazepines); Ba (barbituates); Px (propoxyphene).

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for detecting the presence of one or more non-serologically cross-reactive analyte types in a sample using a competitive homogeneous assay: where the assay detects a plurality of different analyte types that are non-serologically cross-reactive and, where the assay involves analyte and receptor binding pairs such that the presence of one or more different analyte types is determined by enzyme activity reflecting the concentration of analyte when present in excess of a predetermined concentration of the cutoff said method comprising the steps of:
   (I) combining in an aqueous medium:
      (a) glucose-6-phosphate dehydrogenase (G6PDH) analyte binding pair member conjugates, the conjugates comprised of G6PDH covalently linked to a plurality of known analyte binding pair members of which at least two are non-serologically cross-reactive;
      (b) receptors able to bind to each analyte type to be detected and to the G6PDH-analyte binding pair member conjugates; and,
      (c) a sample to be tested for the presence of any of the plurality of analyte types; and,
   (II) detecting increased G6PDH activity in the aqueous medium due to competitive binding of the receptors with the analyte types in the sample where analyte types bind receptors permitting the G6PDH-analyte binding pair member conjugates to exhibit maximal enzyme activity; wherein:
      (i) concentrations of G6PDH-analyte binding pair member conjugates and of the receptors are adjusted in the aqueous mixture so that the enzyme rate at the predetermined cutoff concentrations is approximately the same for the different analyte types whose presence is to be detected;
      (ii) wherein the G6PDH is deactivated by from about 20% to about 85% resulting from the covalent linkage to the analyte binding pair member; and
      (iii) wherein the deactivated G6PDH is inhibited by from about 20% to about 85% when bound to the receptors.

2. A method of claim 1 where at least two of the analyte types have a different cutoff concentration.

3. A method according to claim 1 in which the conjugates comprise individual G6PDH molecules covalently linked to a plurality of different types of analytes.

4. A method according to claim 1 in which the conjugates comprise individual G6PDH molecules covalently linked to a plurality of identical analyte types.

5. A method according to claim 1 in which the analyte types are selected from the group consisting of: licit and illicit drugs, sugars, amino acids, peptides, nucleic acids, nucleosides, nucleotides, vitamins, hormones, steroids, toxins, chemical and biological warfare agents, pesticides, and industrial chemicals.

6. A method according to claim 1 in which the analyte types are selected from the group consisting of: licit and illicit drugs.

7. A method according to claim 1 in which at least two of the analyte types are selected from opium, opioid analgesics, amphetamines, cocaine, methadone, alkaloids, catecholamines, methylendioxyamphetamines phencyclidine, propoxyphene, methaqualone, barbiturates, benzodiazepines, tricyclic antidepressants, tranquilizers, tetrahydrocannabinol, lysergic acid diethylamide, ketamine, and γ-hydroxybutyrate.

8. A method according to claim 7 in which at least two of the analyte types are selected from drugs of abuse having two different predetermined cutoff concentrations.

9. A method according to claim 1 in which at least two of the analyte types are selected from opioid analgesics, amphetamines, cocaine, tetrahydrocannabinol, phencyclidine, methylenedioxyamphetamines, ketamine, lysergic acid diethylamide, ketamine, y-hydroxybutyrate, methadone, methaqualone, and propoxyphene.

10. A method according to claim 1 in which at least two of the analyte types are selected from the group consisting of: barbiturates, tricyclic anti-depressants, tranquilizers, and benzodiazepines.

11. A method according to claim 1 in which at least two of the analyte types are selected from the group consisting of: alkaloids, peptides, nucleic acids, nucleosides, nucleotides, vitamins, hormones, food supplements, sugars, steroids, and amino acids.

12. A method according to claim 1 in which at least two of the analyte types are selected from the group consisting of: chemical and biological warfare agents, toxins, pesticides, herbicides, and industrial chemicals and pollutants.

13. A method according to claim 1 in which the G6PDH is deactivated by from about 20 to about 60%.

14. A method according to claim 1 in which the enzyme activity of the deactivated G6PDH-analyte conjugate is inhibited by from about 40 to about 80%.

15. A method according to claim 1 in which the G6PDH is a recombinant G6PDH.

16. A method according to claim 1 wherein the receptors are antibodies.

* * * * *